US008278049B2

(12) United States Patent
Xie

(10) Patent No.: US 8,278,049 B2
(45) Date of Patent: Oct. 2, 2012

(54) SELECTIVE ENRICHMENT OF CPG ISLANDS

(75) Inventor: Hehuang Xie, Chicago, IL (US)

(73) Assignee: Ann & Robert H. Lurie Children's Hospital of Chicago, Chicago, IL (US)

(*) Notice: Subject to any disclaimer, the term of this patent is extended or adjusted under 35 U.S.C. 154(b) by 19 days.

(21) Appl. No.: 12/767,382

(22) Filed: Apr. 26, 2010

(65) Prior Publication Data
US 2011/0263434 A1 Oct. 27, 2011

(51) Int. Cl.
*C12Q 1/68* (2006.01)
(52) U.S. Cl. .................................... 435/6.11; 435/6.1
(58) Field of Classification Search ................ None
See application file for complete search history.

(56) References Cited

U.S. PATENT DOCUMENTS

| | | | |
|---|---|---|---|
| 4,914,210 A | 4/1990 | Levenson et al. | |
| 4,962,029 A | 10/1990 | Levenson et al. | |
| 5,786,146 A | 7/1998 | Herman et al. | |
| 5,888,723 A | 3/1999 | Sutton et al. | |
| 6,268,490 B1 | 7/2001 | Imanishi et al. | |
| 6,720,411 B2 | 4/2004 | Mirkin et al. | |
| RE39,793 E * | 8/2007 | Brenner ........................ | 536/22.1 |
| 7,425,415 B2 * | 9/2008 | Pfeifer et al. ................ | 435/6.12 |
| 2003/0143604 A1 | 7/2003 | Storhoff | |
| 2005/0053942 A1* | 3/2005 | Kauppinen et al. ............... | 435/6 |
| 2006/0148124 A1 | 7/2006 | Wilson | |
| 2006/0177855 A1 | 8/2006 | Utermohlen | |
| 2009/0036315 A1 | 2/2009 | Labgold | |
| 2009/0233809 A1 | 9/2009 | Faham et al. | |
| 2009/0270482 A1 | 10/2009 | Schuebeler | |

FOREIGN PATENT DOCUMENTS
WO WO 00/26401 5/2000

OTHER PUBLICATIONS

Gnirke et al., Solution hybrid selection with ultra-long oligonucleotides for massively parallel targeted sequencing; Nature Biotech, vol. 27, No. 2, pp. 182-189, 2009.*
Frey et al., PCR-amplification of GC-rich regions: 'slowdown PCR'; Nature Protocols, vol. 3, No. 8, pp. 1312-1317, 2008.*
Chalaya et al Improving specificity of DNA hybridization-based methods; Nucleic Acids Research, vol. 32, No. 16, e130, 2004.*
Southern et al., Analyzing and Comparing Nucleic Acid Sequences by Hybridization to Arrays of Oligonucleotides: Evaluation Using Experimental Models; Genomics, vol. 13, pp. 1008-1017, 1992.*
Cook et al., Systematic Validation and Atomic Force Microscopy of Non-Covalent Short Oligonucleotide Barcode Microarrays; PLoS One, vol. 3, No. 2, e1546, pp. 1-14, 2008.*
Berman et al., "Locking in on the Human Methylome," *Nat. Biotech.*, 27(4):341-342 (2009).
Lister et al., "Human DNA Methylomes at Base Resolution Show Widespread Epigenomic Differences," *Nature*, 462(7271):315-322 (2009).
Hodges et al., "High Definition Profiling of Mammalian DNA Methylation by Array Capture and Single Molecule Bisulfite Sequencing," *Genome Res.*, 19:1593-1605 (2009).
Deng et al., "Targeted Bisulfite Sequencing Reveals Changes in DNA Methylation Associated with Nuclear Reprogramming," *Nat. Biotech.*, 27(4):353-360 (2009).
Ball et al., "Targeted and Genome-Scale Strategies Reveal Gene-Body Methylation Signatures in Human Cells," *Nat. Biotech.*, 27(4):361-368 (2009).
Gu et al., "Genome-Scale DNA Methylation Mapping of Clinical Samples at Single-Nucleotide Resolution," *Nat. Methods*, 7:133-136 (2010).
Gardiner-Garden et al., "CpG Islands in Vertebrate Genomes," *J. Mol. Biol.*, 196:262-282 (1987).
Kuhn et al., "The UCSC Genome Browser Database: Update 2009," *Nucl. Acids Res.*, 37:D755-D761 (2008).
Chien and Davidson, "RNA:DNA Hybrids are More Stable than DNA:DNA Duplexes in Concentrated Perchlorate and Trichloroacetate Solutions," *Nucl. Acids Res.*, 5(5):1627 (1978).
Ray et al., "Peptide Nucleic Acid (PNA): Its Medical and Biotechnical Applications and Promise for the Future," *FASEB J.*, 14:1041-1060 (2000).
Nielsen et al., "An Introduction to Peptide Nucleic Acid," *Curr. Issues Mol. Biol.*, 1(2):89-104 (1999).
Aviv et al., "Purification of Biologically Active Globin Messenger RNA by Chromatography on Oligothymidylic Acid-Cellulose," *PNAS*, 69(2):1408-1412 (1972).
Gonzalgo and Jones, Rapid Quantitation of Methylation Differences at Specific Sites Using Methylation-Sensitive Single Nucleotide Primer Extension (MS-SNuPE), *Nucleic Acids Res.*, 25(12):2529-2531 (1997).
Xiong and Laird, "COBRA: A Sensitive and Quantitative DNA Methylation Assay," *Nucleic Acids Res.*, 25(12):2532-2534 (1997).
Toyota et al., "Identification of Differentially Methylated Sequences in Colorectal Cancer by Methylated CpG Island Amplification," *Cancer Res.*, 59:2307-12 (1999).

(Continued)

*Primary Examiner* — Celine Qian
*Assistant Examiner* — Addison D Ault
(74) *Attorney, Agent, or Firm* — Brinks Hofer Gilson & Lione

(57) ABSTRACT

The present invention provides compositions and methods for selectively enriching genomic CpG island (CGI)- and other epigenetically informative CG-rich polynucleotide targets. The method involves co-incubation of denatured or partially denatured polynucleotide fragments containing the CGI- or CG-targeted region(s) of interest with an oligonucleotide capture pool collectively designed to selectively target CGIs. The oligonucleotide capture pool includes a plurality of different oligonucleotides, each oligonucleotide coupled to a capture tag, whereby the oligonucleotide includes a CpG target sequence restricted to 4 to 10 bases. Upon binding, capture oligonucleotides bound to the target fragments are enriched by separating the bound fragments from the unbound fragments. The enriched fragments may be subjected to further analyses, including bisulfite sequencing to generate a methylation profile at the single nucleotide level.

25 Claims, 6 Drawing Sheets

OTHER PUBLICATIONS

Xie et al., "High-Throughput Sequence-Based Epigenomic Analysis of Alu Repeats in Human Cerebellum," *Nucl. Acids Res.*, 37:4331-4340 (2009).

Cieslak et al., "Thermolytic 4-Methylthio-1-butyl Group for Phosphate/Theiphosphate Protection in Solid-Phase Synthesis of DNA Oligonucleotides," *J. Org. Chem.*, 69:2509-2515 (2004).

Saxonov et al., "A Genome-Wide Analysis of CpG Dinucleotides in Human Genome Distinguishes Two Distinct Classes of Promoters," *PNAS*, 103(5):1412-1417 (2006).

Kandimalla et al., "Design, Biochemical, Biophysical and Biological Properties of Cooperative Antisense Oligonucleotides," *Nucleic Acids Research*, 23(17):3578-3584 (1995).

Armour et al., "Digital Transcriptome Profiling Using Selective Hexamer Priming for cDNA Synthesis," *Nature Methods*, 6(9):647-650 (2009).

Flusberg et al., "Direct Detection of DNA Methylation During Single-Molecule, Real-Time Sequencing," *Nature Methods*, 7(6):461-467 (2010).

Li et al., "Sensitive Digital Quantification of DNA Methylation in Clinical Samples," *Nature Biotechnology*, 27(9):858-865 (2009).

Huang, Q., et al., "Isolation and Enrichment of Human Genomic CpG Islands by Methylation-Sensitive Mirror Orientation Selection," *Analytical Biochemistry*, 365(2):153-164 (May 2007).

Gnirke, A., "Solution Hybrid Selection With Ultra-Long Oligonucleotides for Massively Parallel Targeted Sequencing," *Nature Biotechnology*, 27(2):182-189 (Feb. 2009).

Mamanova, L., "Target-Enrichment Strategies for Next-Generation Sequencing," *Nature Methods*, 7(2):111-118 (Feb. 2010).

Nautiyal, S., "High-Throughput Method for Analyzing Methylation of CpGs in Targeted Genomic Regions," *PNAS*, 107(28):12587-12592 (Jul. 2010).

Weise, A., et al., "High-Throughput Sequencing of Microdissected Chromosomal Regions," *European Journal of Human Genetics*, 18(4):457-462 (Nov. 2010).

Shiraishi, M., et al., "Preferential Isolation of DNA Fragments Associated With CpG Islands," *Proc. Natl. Acad. Sci. USA*, 92(10):4229-4233 (Jan. 1995).

Smith, Z.D., et al., "High-Throughput Bisulfite Sequencing in Mammalian Genomes," *Methods*, 48(3):226-232 (Jul. 2009).

Hodges, E., "High Definition Profiling of Mammalian DNA Methylation by Array Capture and Single Molecule Bisulfite Sequencing," *Genome Research*, 19(9):1593-1605 (Sep. 2009).

International Search Report and Written Opinion dated Sep. 26, 2011 in PCT Application No. PCT/US2011/033853.

\* cited by examiner

| $S_L$ Pool | # Different Oligos Per Pool | Total # sites in 27,639 CGIs | Avg. # sites per 200 bp CGI fragment | # CGI hits | % CGI hits |
|---|---|---|---|---|---|
| S4 | 16 | 4,684,913 | 44.35 | 27,626 | 99.95 |
| S5 | 32 | 3,304,356 | 31.28 | 27,570 | 99.8 |
| S6 | 64 | 2,355,666 | 22.30 | 27,410 | 99.2 |
| S7 | 128 | 1,718,032 | 16.26 | 27,113 | 98.1 |
| S8 | 256 | 1,266,564 | 11.99 | 26,445 | 95.7 |
| S9 | 512 | 941,143 | 8.91 | 25,150 | 91.0 |
| S10 (SEQ ID NO. 6) | 1024 | 708,504 | 6.71 | 23,567 | 85.3 |
| S11 (SEQ ID NO. 7) | 2048 | 537360 | 5.09 | 21,748 | 78.7 |
| S12 (SEQ ID NO. 8) | 4096 | 409511 | 3.88 | 19,589 | 70.9 |
| S13 (SEQ ID NO. 9) | 8192 | 315954 | 2.99 | 17,512 | 63.4 |
| S14 (SEQ ID NO. 10) | 16,384 | 245,214 | 2.32 | 15,505 | 56.1 |
| S15 (SEQ ID NO. 11) | 32,768 | 191,398 | 1.81 | 13,529 | 49.0 |

\* where L = length of each oligonucleotide in the $S_L$ pool where every position in every oligonucleotide is an S (G or C), i.e., S4 = 4-mer pool, S5 = 5-mer pool, etc.

FIG. 1

Position Weight Matrices of CpG Islands with XXCGXX oligonucleotide pool, where X = A, C, G, or T

| Position | A | G | C | T |
|---|---|---|---|---|
| 1 | 13.4 | 35.5 | 36.6 | 14.5 |
| 2 | 11.6 | 38.6 | 37.1 | 12.7 |
| 3 | 0.0 | 0.0 | 100.0 | 0.0 |
| 4 | 0.0 | 100.0 | 0.0 | 0.0 |
| 5 | 12.6 | 37.3 | 38.5 | 11.6 |
| 6 | 14.5 | 36.7 | 35.4 | 13.4 |

FIG. 2A

| Position | A | G | C | T |
|---|---|---|---|---|
| 1 | 15.3 | 36.4 | 33.3 | 15.0 |
| 2 | 14.8 | 33.7 | 37.7 | 13.8 |
| 3 | 13.5 | 35.5 | 36.4 | 14.5 |
| 4 | 11.7 | 38.5 | 37.1 | 12.7 |
| 5 | 0.0 | 0.0 | 100.0 | 0.0 |
| 6 | 0.0 | 100.0 | 0.0 | 0.0 |

FIG. 2B

| Total Number Oligonucleotide Hits Per Capture Pool | Human CpG Islands | Human Genome | Human Genome (CGI Masked) | Human Genome (Repeat Masked) | Human Genome (CGI and Repeat Masked) | Human Repeat Regions |
|---|---|---|---|---|---|---|
| Total bp | 21,129,015 | 2,858,034,764 | 2,836,905,749 | 1,462,675,415 | 1,441,546,400 | 1,395,359,349 |
| # S4 hits | 4,684,913 | 65,544,185 | 60,859,272 | 33,812,459 | 24,442,633 | 31,731,726 |
| # S5 hits | 3,304,356 | 27,469,426 | 24,165,070 | 14,399,923 | 11,095,567 | 13,069,503 |
| # S6 hits | 2,355,666 | 12,928,808 | 10,573,142 | 6,754,110 | 4,398,444 | 6,174,698 |
| # S7 hits | 1,718,032 | 6,786,070 | 5,068,038 | 3,740,105 | 2,022,073 | 3,045,965 |
| # S8 hits | 1,266,564 | 3,967,191 | 2,700,627 | 2,032,076 | 765,512 | 1,935,115 |
| # S9 hits | 941,143 | 2,456,512 | 1,515,369 | 1,230,582 | 289,439 | 1,225,930 |
| # S10 (SEQ ID NO. 6) hits | 708,504 | 1,591,757 | 883,253 | 771,822 | 63,318 | 819,935 |
| # SCGS hits | 1,193,917 | 8,044,779 | 6,850,862 | 3,926,110 | 2,732,193 | 4,118,669 |
| # S(1)CGS(2) hits | 861,271 | 4,846,115 | 3,984,844 | 2,200,568 | 1,339,297 | 2,645,547 |
| # S(2)CGS(2) hits | 624,723 | 3,143,432 | 2,518,709 | 1,315,327 | 690,604 | 1,828,105 |
| # S(2)CGS(3) hits | 455,941 | 1,603,155 | 1,147,214 | 768,700 | 312,759 | 834,455 |
| # S(3)CGS(3) hits | 336,804 | 932,294 | 595,490 | 472,943 | 136,139 | 459,351 |
| # S(3)CGS(4) hits | 247,292 | 552,021 | 304,729 | 290,593 | 43,301 | 261,428 |
| # S(4)CGS(4) (SEQ ID NO. 12) hits | 184,119 | 347,051 | 162,932 | 184,181 | 62 | 162,870 |

FIG. 3A

| Average Number of Oligonucleotide Hits Per 200 bp | Human CpG Islands (CGI) | Human Genome | Human Genome (CGI Masked) | Human Genome (CGI and Repeat Masked) | Human Repeat Regions | CGI to CGI Masked Genome Ratio | CGI to CGI and Repeat Masked Genome Ratio |
|---|---|---|---|---|---|---|---|
| Total bp | 21,129,015 | 2,858,034,764 | 2,836,905,749 | 1,441,546,400 | 1,395,359,349 | | |
| S4 | 44.35 | 4.59 | 4.29 | 4.04 | 4.55 | 10.3 | 11.0 |
| S5 | 31.28 | 1.92 | 1.70 | 1.54 | 1.87 | 18.4 | 20.3 |
| S6 | 22.30 | 0.90 | 0.75 | 0.61 | 0.89 | 29.9 | 36.5 |
| S7 | 16.26 | 0.47 | 0.36 | 0.28 | 0.25 | 45.5 | 58.0 |
| S8 | 11.99 | 0.28 | 0.19 | 0.11 | 0.18 | 63.0 | 112.9 |
| S9 | 8.91 | 0.17 | 0.11 | 0.04 | 0.18 | 83.4 | 221.8 |
| S10 (SEQ ID NO. 6) | 6.71 | 0.11 | 0.06 | 0.01 | 0.12 | 107.7 | 763.4 |
| SCGS | 11.30 | 0.56 | 0.48 | 0.38 | 0.59 | 23.4 | 29.8 |
| S$_{(1)}$CGS$_{(2)}$ | 8.15 | 0.34 | 0.28 | 0.19 | 0.38 | 29.0 | 43.9 |
| S$_{(2)}$CGS$_{(2)}$ | 5.91 | 0.22 | 0.18 | 0.10 | 0.26 | 33.3 | 61.7 |
| S$_{(2)}$CGS$_{(3)}$ | 4.32 | 0.11 | 0.08 | 0.04 | 0.12 | 53.4 | 99.5 |
| S$_{(3)}$CGS$_{(3)}$ | 3.19 | 0.07 | 0.04 | 0.02 | 0.05 | 75.9 | 168.8 |
| S$_{(3)}$CGS$_{(4)}$ | 2.34 | 0.04 | 0.02 | 0.01 | 0.04 | 109.0 | 389.6 |
| S$_{(4)}$CGS$_{(4)}$ (SEQ ID NO. 12) | 1.74 | 0.02 | 0.01 | 0.00 | 0.02 | 151.7 | 202,607.9 |

FIG. 3B

| Oligo Conc | 4-mer Tm GCGC | 5-mer Tm GCGCG | 6-mer Tm CGCGCG | 7-mer Tm CCGCGCG | 8-mer Tm CCGGCGCGG | 9-mer Tm CGCGGCGCGG | 10-mer Tm CGCGCGGCGCG (SEQ ID NO. 51) |
|---|---|---|---|---|---|---|---|
| 200 µM | 25.4 °C | 47.8 °C | 56.4 °C | 66.9 °C | 70.3 °C | 78.8 °C | 80.9 °C |
| 100 µM | 21.3 °C | 44.3 °C | 53.5 °C | 64.2 °C | 67.9 °C | 76.4 °C | 79.0 °C |
| 50 µM | 17.4 °C | 40.9 °C | 50.6 °C | 61.6 °C | 65.5 °C | 74.3 °C | 77.1 °C |
| 20 µM | 12.3 °C | 36.5 °C | 46.9 °C | 58.1 °C | 62.3 °C | 71.5 °C | 74.6 °C |
| 10 µM | < 10 °C | 33.3 °C | 44.1 °C | 55.5 °C | 60.0 °C | 69.4 °C | 72.8 °C |
| 5 µM | < 10 °C | 30.1 °C | 41.4 °C | 53.0 °C | 57.7 °C | 67.3 °C | 71.0 °C |

FIG. 4

SEQUENCE LISTING

<160> NUMBER OF SEQ ID NOS: 12

<210> SEQ ID NO 1
<211> LENGTH: 10
<212> TYPE: DNA
<213> ORGANISM: Artificial Sequence

```
<220> FEATURE:
<223> OTHER INFORMATION: probe

<400> SEQUENCE: 1
cgcgcgcgcg                                                                10

<210> SEQ ID NO 2
<211> LENGTH: 23
<212> TYPE: DNA
<213> ORGANISM: Artificial Sequence
<220> FEATURE:
<223> OTHER INFORMATION: adaptor
<220> FEATURE:
<221> NAME/KEY: misc_feature
<222> LOCATION: (23)..(23)
<223> OTHER INFORMATION: 3' linked to 2'-3'-dideoxycytidine

<400> SEQUENCE: 2
gagagtggaa gaaagtccac tct                                                 23

<210> SEQ ID NO 3
<211> LENGTH: 49
<212> TYPE: DNA
<213> ORGANISM: Artificial Sequence
<220> FEATURE:
<223> OTHER INFORMATION: primer

<400> SEQUENCE: 3
ctgccccggg ttcctcattc tcttcaaaaa taaactttct tccactctc                     49

<210> SEQ ID NO 4
<211> LENGTH: 41
<212> TYPE: DNA
<213> ORGANISM: Artificial Sequence
<220> FEATURE:
<223> OTHER INFORMATION: adaptor
<220> FEATURE:
<221> NAME/KEY: misc_feature
<222> LOCATION: (41)..(41)
<223> OTHER INFORMATION: 3' linked to 2'-3'-dideoxycytidine

<400> SEQUENCE: 4
atcaccgact gcccatagag aggaaagcgg aggcgtagtg g                             41

<210> SEQ ID NO 5
<211> LENGTH: 41
<212> TYPE: DNA
<213> ORGANISM: Artificial Sequence
<220> FEATURE:
<223> OTHER INFORMATION: adaptor

<400> SEQUENCE: 5
ccactacgcc tccgctttcc tctctatggg cagtcggtga t                             41

<210> SEQ ID NO 6
<211> LENGTH: 10
<212> TYPE: DNA
<213> ORGANISM: Artificial Sequence
<220> FEATURE:
<223> OTHER INFORMATION: probe

<400> SEQUENCE: 6 ssssssssss                                                                10

<210> SEQ ID NO 7
<211> LENGTH: 11
<212> TYPE: DNA
<213> ORGANISM: Artificial Sequence
```

```
<220> FEATURE:
<223> OTHER INFORMATION: probe

<400> SEQUENCE: 7
ssssssssss s                                                            11

<210> SEQ ID NO 8
<211> LENGTH: 12
<212> TYPE: DNA
<213> ORGANISM: Artificial Sequence
<220> FEATURE:
<223> OTHER INFORMATION: probe

<400> SEQUENCE: 8
ssssssssss ss                                                           12

<210> SEQ ID NO 9
<211> LENGTH: 13
<212> TYPE: DNA
<213> ORGANISM: Artificial Sequence
<220> FEATURE:
<223> OTHER INFORMATION: probe

<400> SEQUENCE: 9
ssssssssss sss                                                          13

<210> SEQ ID NO 10
<211> LENGTH: 14
<212> TYPE: DNA
<213> ORGANISM: Artificial Sequence
<220> FEATURE:
<223> OTHER INFORMATION: probe

<400> SEQUENCE: 10
ssssssssss ssss                                                         14

<210> SEQ ID NO 11
<211> LENGTH: 15
<212> TYPE: DNA
<213> ORGANISM: Artificial Sequence
<220> FEATURE:
<223> OTHER INFORMATION: probe

<400> SEQUENCE: 11
ssssssssss sssss                                                        15

<210> SEQ ID NO 12
<211> LENGTH: 10
<212> TYPE: DNA
<213> ORGANISM: Artificial Sequence
<220> FEATURE:
<223> OTHER INFORMATION: probe

<400> SEQUENCE: 12 sssscgssss                                                              10
```

SELECTIVE ENRICHMENT OF CPG ISLANDS

FIELD OF THE INVENTION

The present invention relates to compositions and methods for selectively enriching genomic target fragments containing CpG island and other epigenetically informative CG rich regions, and subsequent methods for analyzing the methylation status of the enriched fragments.

BACKGROUND

DNA methylation, the only covalent modification of DNA, involves the addition of a methyl group to the 5 position of the cytosine pyrimidine ring or the number 6 nitrogen of the adenine purine ring. Methylated DNA has been found in bacteria, fungi, plant and mammalian genomes. In vertebrates, including mammals, DNA methylation primarily occurs on the cytosine in CpG dinucleotide. Approximately 60-90% of CpG dinucleotides are methylated in most mammalian cell types. The CpG dinucleotides are not uniformly distributed in mammalian genomes. Short regions of DNA with high frequency of 5'-CG-3' (CpG) dinucleotides are called CpG islands. For example, sequence analysis of the human genome has estimated nearly 30,000 CpG islands, which accounts for about 0.7% of the genome. CpG dinucleotides in the remaining 99.3% of the genome are sparsely distributed. Because of the high cytosine-guanine frequency of CpG islands, it is possible to identify them without knowledge of the methylation pattern of the DNA.

CpG islands often harbor the promoters of genes and play a pivotal role in the control of gene expression. In normal tissue, CpG islands are usually unmethylated but a subset of islands becomes methylated during oncogenesis, cellular development, and various disease states. Accordingly, there is great interest in determining the methylation status or profiles of promoters and CpG islands (CGIs) in various tissues, especially with regard to methylation differences accounting for altered patterns of expression in normal development and in various disease states which would greatly improve our understanding of these processes and provide potential diagnostic markers and therapeutic targets for diseases (Berman et al., Nat. Biotech., 27:341-342, 2009).

Bisulfite sequencing remains the "gold standard" for generating methylation data at single-base resolution. One way to obtain such methylation data for the CGIs is to sequence entire epigenome directly. Due to the difficulty in mapping bisulfite converted sequence reads and the methylation heterogeneity in a cell population, approximately 100 gigabases (Gb) sequence data would be needed to generate a high-resolution human DNA methylation map (Lister et al., Nature, 462:315-322, 2009). Other methylation profiling approaches include array capture (Hodges et al., Genome Res., 19:1593-1605, 2009), padlock probe capture (Deng et al., Nat. Biotech., 27:353-360, 2009; Ball et al., Nat. Biotech., 27:361-368, 2009) and reduced representation bisulfite sequencing (Gu et al., Nat. Methods, 7:133-136, 2010), which have been employed to target over 300, 2000 and 15,000 CGIs, respectively.

There is a need for simple and efficient means for selective enrichment of CGI- and other epigenetically informative CG-rich polynucleotides. When applied to epigenetic studies of methylation, the present invention has several advantages. Compared to the above-described methylation profiling approaches, the present invention provides a fast, cost-effective, PCR-free means for generating epigenome maps at single nucleotide resolution. Instead of enzyme digestion, the use of sonicated DNA improves evaluation of CpG dinucleotides in the epigenome that might otherwise go undetected. Further, since the enrichment is performed before bisulfite conversion, no bias against methylation status is introduced. Finally, the present method is designed to enable consistent yields and broad coverage of CGIs and individual CpG sites.

SUMMARY

The present invention provides compositions and methods for selectively enriching genomic target fragments containing CpG island (CGIs) and other epigenetically informative CG rich regions. The invention employs short oligonucleotides overrepresented in CGIs to allow for multiple oligonucleotide bindings to facilitate selective enrichment. The inventive method involves co-incubation of denatured or partially denatured polynucleotide fragments containing targeted CpG island region fragments with an oligonucleotide capture pool collectively designed to selectively target CGIs. The oligonucleotide capture pool includes a plurality of different oligonucleotides, each oligonucleotide containing a CpG target sequence restricted to 4 to 10 bases and coupled to a capture tag, which may include, for example, a nanoparticle, biotin, or combination thereof. A spacer may be included between the oligonucleotide and the capture tag.

In one embodiment, the capture oligonucleotides are suspended and freely diffusible in solution during hybridization to polynucleotides. In another embodiment, the capture oligonucleotides may be bound to a matrix in a column, whereby the polynucleotide fragments are bound to the oligonucleotides in the column and eluted therefrom. Upon targeted binding of the capture oligonucleotides to CGI-containing fragments, the targeted fragments are enriched by separating them from the unbound polynucleotide fragments. Oligonucleotides in the capture pool may include conventional deoxyribonucleotides or ribonucleotides. In addition, one or more of the oligonucleotides may include unconventional nucleic acids, including locked nucleic acids (LNAs) and peptide nucleic acids (PNAs).

The oligonucleotide capture pool is designed to collectively and selectively target and enrich for CpG island-containing fragments, which can be isolated and subjected to further analyses, including bisulfite sequencing to generate a methylation profile at the single nucleotide level.

In another aspect, the invention provides an oligonucleotide capture pool configured to collectively and selectively enrich for CpG island-containing DNA fragments present in a fragmented pool of genomic DNA fragments, whereby the oligonucleotide capture pool contains a plurality of different capture oligonucleotides, each capture oligonucleotide being coupled to a capture tag and having a CpG target sequence or capture oligonucleotide 4 to 10 bases in length, where at least 60% of the collective bases in the CpG target sequences of the capture pool are cytosine or guanine. The capture tag may include, for example, a nanoparticle, biotin, or combination thereof.

In a particular embodiment, each CpG target sequence or capture oligonucleotide in the capture pool is between 5 to 8 bases in length. In addition, the collective percentage of cytosine and guanine bases in the CpG target sequences in the capture pool or in the capture oligonucleotides as a whole may be at least 70%, at least 80%, at least 90%, at least 95%, or 100%. Further, each CpG target sequence or capture oligonucleotide in the capture pool may have a uniform CpG target sequence length (L) equal to between 4 to 10 bases in length. Moreover, the number (P) of different capture oligonucleotides in the pool may defined by the formula $P=2^L$.

In one embodiment, every nucleotide in each oligonucleotide in the capture pool is cytosine or guanine, the 3'-terminal dinucleotide in each oligonucleotide is CG, and each CpG target sequence is between 5 to 8 bases in length. In another embodiment, each oligonucleotide in the capture pool may include a consecutive run of cytosine or guanine residues spanning the middle of the CpG target sequence.

In a further aspect, the CpG target sequences in the capture pool may be designed in accordance with a progressive scanning analysis of CpG island DNA sequences in a given species genome, where the target sequences reflect their composition in the CpG island DNA sequences. Thus, in one embodiment, each oligonucleotide in the capture pool includes at least one CG dinucleotide, where the cytosine nucleotide in the CG dinucleotide is positioned in the middle of the CpG target sequence or in a position immediately 5' to the middle of the CpG target sequence. In another embodiment, each oligonucleotide in the capture pool contains a CG dinucleotide at the 3'-end. In yet another embodiment, each oligonucleotide in the capture pool includes a CpG target sequence L bases in length that is restricted to cytosine or guanine residues (i.e., GC-restricted) such that the scanning analysis selects GC-restricted oligonucleotide target sequences for the capture pool that represent the top 50%, the top 30%, or the top 10% of GC-restricted oligonucleotides L bases in length that are present in the CpG islands.

Capture oligonucleotide in the capture pool may include at least one nucleotide selected from the group consisting of DNA, RNA, LNA, and PNA. In addition, one or more of the capture oligonucleotides in the capture pool may contain a spacer.

The recovered CGI- or CG-rich fragments may be subjected to various analyses, whereby short oligonucleotides are used to enrich for CGI- and/or other epigenetically informative CG-rich fragments, which are then subjected to any one of the art-recognized approaches for determining their methylation status as further described below.

BRIEF DESCRIPTION OF THE DRAWINGS

FIG. 1 depicts the total number of oligonucleotide binding sites in all 27,639 human CpG islands (CGIs) in the UCSC CpG island database relative to a range of different oligonucleotide capture pools containing oligonucleotides restricted to cytosine or guanine (S) and represented by $S_L$, where L=length of oligonucleotide in bases, and $P=2^L$ is equal to the total number of different oligonucleotides in each pool. FIG. 1 also shows the average number of oligonucleotide binding sites per every 200 bp fragment, and the total number and percentage of human CGIs that can be collectively targeted by a given $S_L$ pool.

FIG. 2A depicts a position weight matrix analysis table showing the frequencies of nucleotides in positions surrounding a central CG core dinucleotide in a hexamer (6-mer) pool when scanning across all 27,639 CGIs in the UCSC CpG island database.

FIG. 2B depicts a position weight matrix analysis table showing the frequencies of nucleotides 5' of a 3-terminal CG dinucleotide in a hexamer (6-mer) pool when scanning across all 27,639 CGIs in the UCSC CpG island database.

FIG. 3A depicts the total number of oligonucleotide "hits" or binding sites collectively represented by different oligonucleotide capture pools, whereby the "hits" are defined by the number of times an oligonucleotide sequence from a given capture pool is present in: (1) all 27,639 CGIs in the UCSC CpG island database; (2) in the human genome as a whole; (3) in the human genome following subtraction of the CGIs (CGI masked); (4) in the human repeat regions; (5) in the human genome following subtraction of the repeat regions (repeat masked); (6) in the human genome following subtraction of CGIs and repeats (CGI and repeat masked). Pools S4 to S10 are restricted to G and C residues as described above. The remainder of the pools are defined by the formula, 5'-S(1-4)-C-G-S(1-4)-3', whereby S(1-4) represents stretches of 1 to 4 C or G nucleotides flanking a CG dinucleotide based on nucleotide position frequencies obtained by scanning across all 27,639 CGIs in the UCSC CpG island database as described above.

FIG. 3B depicts the average number of oligonucleotide hits per 200 bp fragment mapping to the five of the six regions described in FIG. 3A. The last two columns in FIG. 3B highlight the selectivity of binding to CpG island fragments relative to non-CpG island fragments, as reflected in the ratio of oligonucleotides binding to CpG islands as opposed to non-CpG island regions.

FIG. 4 depicts melting temperatures for GC-restricted oligonucleotides as function of oligonucleotide length and oligonucleotide concentration.

DETAILED DESCRIPTION

Figure 5:
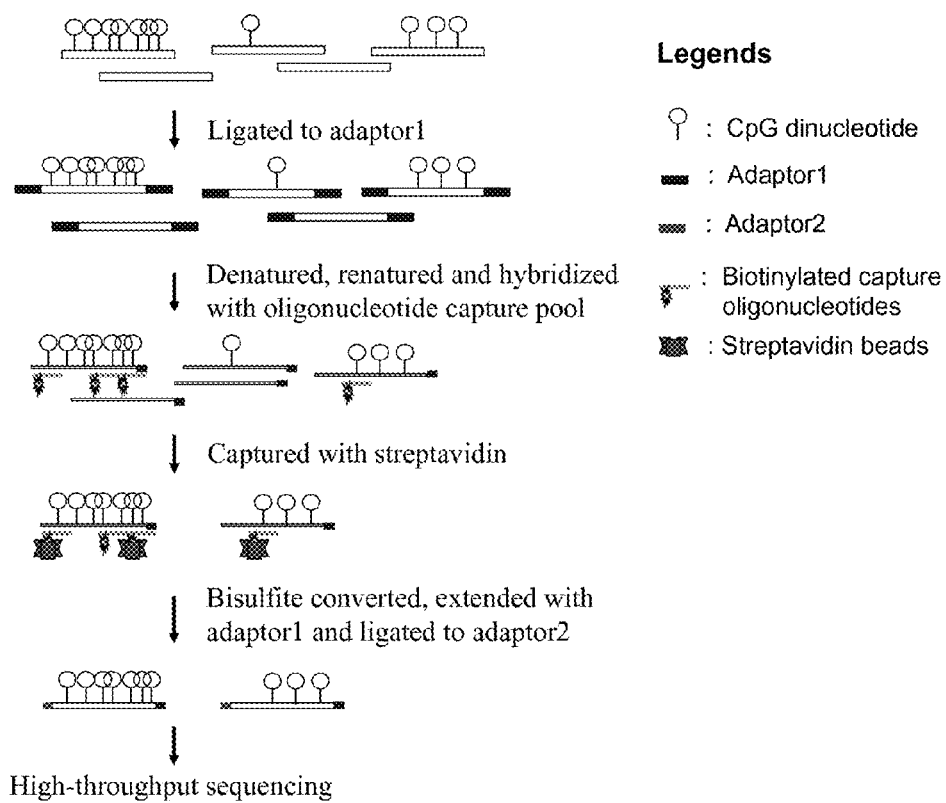
FIG. 5 depicts a flow diagram of bisulfite sequencing of oligonucleotide-captured CpG enriched regions (bSOCCER).

In order to provide a clear and consistent understanding of the specification and claims, the following definitions are provided.

Units, prefixes, and symbols may be denoted in their SI accepted form. Unless otherwise indicated, nucleic acids are written left to right in 5' to 3' orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic acid sequence discrepancy within the application, the figures control.

As used herein, the term "CpG island" refers to a contiguous region of genomic DNA that satisfies the criteria of (1) having a frequency of CpG dinucleotides corresponding to an "observed/expected ratio" greater than 0.6; (2) having a "GC Content" greater than 0.5; and (3) have a length of at least 0.2 kb (as described in Gardiner-Garden et al., J. Mol. Biol., 196:262-282, 1987), with the exception that repeat regions matching these criteria are excluded (or masked).

The term "observed/expected ratio" refers to the frequency of CpG dinucleotides within a particular DNA fragment or sequence, and corresponds to the [number of CpG sites/(number of C bases×number of G bases)]×DNA length (in bases) for each fragment or sequence area evaluated (as described in Gardiner-Garden et al., J. Mol. Biol., 196:262-282, 1987).

The terms "CpG island fragment" or "CGI fragment" are used interchangeably to refer to a polynucleotide fragment mapping to and containing at least part of a CpG island.

As used herein, the term "capture oligonucleotide" refers to an oligonucleotide comprising a CpG target sequence between 4 and 10 bases in length, coupled to a capture tag, and optionally coupled to a nucleotidyl or non-nucleotidyl spacer.

The term "CpG target sequence" refers to a stretch of stretch of bases targeted to selectively enrich for CpG island fragments and/or other methylation informative CG-rich fragments.

The terms "oligonucleotide capture pool", "capture pool", and "pool" are used interchangeably to refer to a plurality of capture oligonucleotides, each oligonucleotide containing a specified CpG target sequence, the pool reflecting a range of different CpG target sequences. As used herein, capture oligonucleotides in a capture pool may include a nucleotidyl or non-nucleotidyl spacer.

The term "capture tag" refers to any compound, complex, molecule, or entity, such as an antibody, peptide, nucleic acid, lectin or similar material, that is capable of selectively and specifically binding to an immobilization substrate.

The term "spacer" refers to a structural moiety allowing spatial separation between the CpG target sequence and the capture tag and/or between the CpG target substrate and a solid substrate to the which the capture oligonucleotides are bound, such as nanoparticles, chromatographic beads, or a microarray substrate so as to preserve the functional properties of the individual members on either side of the spacer.

The term "nucleotidyl spacer" refers to a consecutive stretch of all adenine residues or all thymine residues, the nucleotidyl spacer being distinct from the CpG target sequence.

The phrase "collectively designed to selectively target a CpG island" refers to an oligonucleotide capture pool containing capture oligonucleotides having a nucleotide composition collectively designed to selectively enrich one or more CpG islands relative to other genomic regions by a factor of at least 2-fold.

The phrase "progressive scanning analysis" refers to an analysis of CpG islands with respect to the composition and/or proportional number of occurrences for short oligonucleotides, 4 to 10 bases in length when progressively scanning CGI regions for one or more candidate target sequence(s) of interest. Scanning analysis may be used for generating or assembling an oligonucleotide capture pool reflecting the CpG sequences in the targeted CGIs or CG-rich regions, which are incorporated into the oligonucleotide target sequences in the capture pool. Results from the analysis may be expressed in a table reflecting the frequencies of each base in a degenerate target sequence obtained when progressively scanning the CGIs. Alternatively, the results may be expressed in terms of the number of occurrences for each of a plurality of short oligonucleotide sequences when progressively scanning the CpG islands one base at a time, independent of any specific target sequence, or when specifically scanning the CGIs for specific candidate target sequences.

The term "immobilization substrate" refers to any material to which capture tags can be immobilized as described herein. An immobilization substrate has a complementary structural component capable of binding to the capture tag in a capture oligonucleotide, and can facilitate the separation or pull-down of capture oligonucleotides in a sample. Immobilization substrates include but are not limited to streptavidin, fragments of avidin, magnetic beads, as described herein.

The term "enrichment factor" and "level of enrichment" refer to a ratio reflecting the nucleotide content (as a function of total nucleotide bases) of targeted CGI- or CG-rich polynucleotide fragments recovered relative to non-targeted polynucleotide fragments recovered.

The term "hybridization" refers to a bond of an oligonucleotide or polynucleotide to a complementary sequence via Watson-Crick base pairings or other non-natural pairings (where modified oligonucleotides are used) to form a duplex structure, or optionally, a triplex structure when using peptide nucleic acids under certain conditions.

The term "solution phase hybridization conditions" refers to a hybridization reaction occurring where capture oligonucleotides are suspended and freely diffusible in solution during hybridization to polynucleotides. Solution phase hybridization conditions may include conditions where the capture oligonucleotides are attached to nanoparticles that are suspended and freely diffusible in solution (as in a flowable slurry) during hybridization. Solution phase hybridization conditions are distinguished from solid phase capture of hybrids onto an immobilization substrate.

The term "solid phase hybridization conditions" refers to a hybridization reaction occurring where capture oligonucleotides are immobilized on a substrate during hybridization to polynucleotides. The substrate may comprise a microarray or stationary beads loaded in a column.

The term "nanoparticle" refers to a small, composite, and/or hollow materials onto which a which a capture oligonucleotide can be attached or immobilized, less than 1 micrometers in diameter or length, less than 200 nanometers, less than about 50 nanometers, or between about 10 to 30 nm in diameter or length. As used herein, a nanoparticle may include a microbead, bead, or any other type of solid or hollow sphere, ball, bearing, cylinder, or other similar configuration of similar size, which may be composed of polymeric, metallic, and/or ceramic material or similar material onto which a capture oligonucleotide can be attached or immobilized. Exemplary nanoparticles may be comprised of a variety of materials, including but not limited to an elemental metals, semiconductor materials, polymeric materials, metal oxides, gold, titanium, $TiO_2$, tin, $SnO_2$, indium tin oxide (ITO), conductive metal oxides, conductive polymers, other conductive substances, and combinations thereof.

The term "microarray" refers to any art-recognized "nucleic acid microarray", including but not limited to DNA microarrays and 'DNA chips," and encompasses all art-recognized solid supports, and encompasses all methods for ordered arrangement and affixing of nucleic acid molecules thereto or synthesis of nucleic acids thereon.

The term "methylation assay" refers to any assay for determining the methylation status of one or more CpG dinucleotide sequences within one or more DNA sequences.

The terms "methylation state" or "methylation status" refer to a determination of the presence or absence of 5-methylcytosine ("5-mCyt") or any other DNA methylation modification at one or a plurality of CpG dinucleotides within a DNA sequence by a methylation assay. The methylation status of a particular DNA fragment or sequence can indicate the methylation state of every base in the sequence or can indicate the methylation state of a subset of the base pairs (e.g., whether the base is cytosine or 5-methylcytosine) within the sequence. Methylation states at one or more particular CpG methylation sites (each having two CpG dinucleotide sequences) within a DNA sequence may include "unmethylated," "fully-methylated" and "hemi-methylated" sites. Methylation status can also indicate information regarding regional methylation density within the sequence without specifying the exact location at the single nucleotide position level.

The term "methylation profile" refers to a set of data representing the methylation states of one or more loci within a molecule of DNA from e.g., the genome of an individual or cells or tissues from an individual. The profile can indicate the methylation state of every base in an individual, can have information regarding a subset of the base pairs (e.g., the methylation state of specific promoters or quantity of promoters) in a genome, or can have information regarding regional methylation density of one or more loci with or without specifying the exact location at the single nucleotide position level.

The term "bisulfite conversion" refers to a biochemical process for converting unmethylated cytosine to uracil, whereby methylation cytosine residues are preserved. Exemplary reagents for bisulfite conversion include sodium bisulfite and magnesium bisulfite.

The term "bisulfite reagent" refers to a reagent comprising bisulfite, disulfite, hydrogen sulfite or combinations thereof, useful as disclosed herein to distinguish between methylated and unmethylated CpG dinucleotide sequences.

In one embodiment, the present invention provides a method for selectively enriching genomic target fragments containing CpG islands (CGIs) and other epigenetically informative CG-rich regions. The method requires a source of polynucleotide fragments containing CGIs, such as sheared genomic DNA, along with an oligonucleotide capture pool comprised of a plurality of capture oligonucleotides. The oligonucleotide capture pool is collectively designed to selectively target the CGIs. Each oligonucleotide in the capture pool includes a CpG target sequence restricted to 4 to 10 bases and is coupled to a capture tag. The length of the capture oligonucleotides may also be restricted to 4 to 10 bases, or they may additionally include a non-nucleotidyl spacer, or a nucleotidyl spacer limited to a stretch of adenine or thymine residues. Polynucleotide fragments are denatured to form a plurality of denatured polynucleotide fragments. The denatured polynucleotide targets are incubated with the oligonucleotide capture pool under conditions sufficient to promote binding of the capture oligonucleotides to polynucleotide fragments corresponding to the targeted CGIs. Targeted CGI fragments bound to the capture oligonucleotides are separated from the unbound polynucleotide fragments and then subjected to further analysis as described below.

The separation of bound fragments from unbound fragments is facilitated by the capture tag, any suitable compound, complex, molecule, or entity, such as antibody, peptide, nucleic acid, lectin or similar material, that is capable of selectively and specifically binding to an immobilization substrate of interest. The capture tag may be nucleotidyl or non-nucleotidyl in nature. However, the nucleic acids in a nucleotidyl capture tag are to be distinguished from the CpG target sequences of the present invention. The capture tags in the capture oligonucleotides may be bound to the immobilization substrate before binding to the genomic polynucleotide fragments or they may be bound to the immobilization substrate following binding of the capture oligonucleotides to the genomic polynucleotide fragments. In a preferred embodiment, the capture oligonucleotide is coupled to a non-nucleotidyl capture tag, such as biotin, a nanoparticle, or combination thereof. Capture oligonucleotides may optionally include or be linked to a spacer which may reduce steric hindrance effects negatively affecting binding of polynucleotides to short capture oligonucleotides when affixed to a solid support, or that may impede simultaneous binding of short capture oligonucleotides to both an immobilization substrate and a target CGI polynucleotide (when using a capture tag such as biotin, for example). Thus, the capture oligonucleotides may include a suitable spacer between the capture tag and the oligonucleotide or between the solid support and the oligonucleotide.

Targeted CGI fragments bound to the capture oligonucleotides may be separated from unbound polynucleotide fragments, for example, using biotinylated capture oligonucleotides bound to polynucleotide targets, whereby oligonucleotide: CGI polynucleotide target hybrids are captured via the capture tag onto streptavidin beads and subsequently released therefrom.

In a particular embodiment, the present invention provides a method to facilitate selective enrichment and analysis of CGI and other CG-rich fragments. The method requires a source of polynucleotide fragments containing CGIs. The polynucleotide fragments are denatured to form a plurality of denatured polynucleotide fragments, which are incubated with a CG-rich oligonucleotide capture pool under conditions sufficient to promote binding of capture oligonucleotides to polynucleotide fragments containing CGIs. The CG-rich capture pool may include GC-rich capture oligonucleotides, whereby the capture pool is designed to collectively and selectively target CGIs. Each oligonucleotide in the capture pool contains a CpG target sequence restricted to 4 to 10 bases, which is coupled to a capture tag, whereby at least 60% of the collective bases in the CpG target sequences in the incubated capture pool are cytosine or guanine. Upon binding the capture oligonucleotides to the targeted polynucleotide fragments, target fragments bound to the capture oligonucleotides are separated from the unbound polynucleotide fragments, using, for example biotinylated capture oligonucleotides recovered from streptavidin beads. Bound CGI-island enriched target fragments may be then subjected to further analysis as described below.

Applicants have surprisingly discovered short capture oligonucleotides containing a CpG target sequence restricted to 4 to 10 bases and coupled to a capture tag for targeting and enrichment of CGI- and other CG-rich fragments. Conventional nucleic acid hybridizations, as used in microarrays, for example, typically utilize polynucleotide probes or oligonucleotide probes that are at least 20-40 bases in length. Shorter oligonucleotides having lower melting temperatures exhibit less stable binding to complementary polynucleotides, as compared to longer oligonucleotides typically used in the art. Applicants have unexpectedly discovered that short oligonucleotides, including oligonucleotides between 4 to 10 bases in length may be utilized for enrichment of CGIs from highly complex genomic fragment populations, including the human genome and its complex composition of nearly 3 billion base pairs. Although not wishing to be bound by theory, it is believed that the genomic regions can be selectively enriched through the use and design of short capture oligonucleotides increasing the frequency of multiple bindings to genomic fragments containing CpG islands, whereby an increased number of oligonucleotide binding sites overcomes the negative effects of lower stability and reduced melting temperature properties of individual short oligonucleotides that would otherwise reduce capture tag-mediated pull-down and enrichment of CG-rich polynucleotides onto a complementary immobilization substrate. Likewise, it is believed that to the extent that non-CpG island regions are less likely to contain multiple binding sites for short CGI-targeted oligonucleotides of the present invention, polynucleotide fragments from these regions are less likely to offer sufficiently stable binding conditions to facilitate pull-down and enrichment of these non-targeted polynucleotide fragments.

Accordingly, in one aspect, the present invention provides oligonucleotide capture pools containing a plurality of different capture oligonucleotides for collectively and selectively enriching CGI- and other epigenetically informative CG-rich target fragments. The oligonucleotide capture pool includes a plurality of capture oligonucleotides, each capture oligonucleotide in the pool containing a CpG target sequence restricted to 4 to 10 bases, whereby each of the oligonucleotides in the capture pool is coupled to a capture tag. The capture oligonucleotides and/or CpG target sequences in a given capture pool may range in size between any one of 4 to 10 bases, including between 5 to 10 bases, between 6 to 10 bases, between 6 to 9 bases, between 5 to 8 bases, between 6 to 8 bases etc. All of the oligonucleotides in the capture pool may share the same length. Accordingly, all of the oligonucleotides in the capture pool may be 4, 5, 6, 7, 8, 9, or bases in length. Alternatively, the capture pool may contain two or more oligonucleotides differing in length. The capture pool may contain a range of different capture oligonucleotides collectively biased in composition to target CGIs and other CG-rich regions.

In one embodiment, this oligonucleotide pool contains capture oligonucleotides, each capture oligonucleotide in the pool containing a CpG target sequence restricted to 4 to 10 bases and having a collective G+C content relative to the CpG target sequence or the oligonucleotide as a whole of at least 60%, at least 70%, at least 80%, at least 90%, or 100%, whereby each of the oligonucleotides in the capture pool is coupled to a capture tag. A CGI- or CG-targeted oligonucleotide capture pool may be distinguished from other short oligonucleotide pools unable to be used for selective enrichment of CpG islands or epigenetically informative CG-rich regions, whereby each position is generic for A, C, G, or T, or contains A, C, G, or T in substantially equivalent amounts at each position relative to the overall pool. Thus, the CG-targeted oligonucleotide capture pool may exclude, for example, members of a capture oligonucleotide subpool comprising 4 to 10 consecutive adenine or thymine bases, whereby each capture oligonucleotide in the subpool is restricted to adenine or thymine bases. Accordingly, the present invention preferably excludes a capture pool containing between any one of 4 to 10 bases, whereby the pool as a whole contains substantially equivalent amounts of adenine, guanine, cytosine, and thymine (or uracil in place of thymine when using RNA oligonucleotides) bases.

In one embodiment, the oligonucleotide capture pool contains between 8 and 1024 different capture oligonucleotides. In another embodiment, the oligonucleotide capture pool contains between 16 and 256 or between 32 and 256 different capture oligonucleotides.

In another embodiment, every nucleotide in the oligonucleotide pool is either cytosine or guanine (S), whereby the length of each oligonucleotide is 4, 5, 6, 7, 8, 9, or 10 bases in length (L), and wherein the number (P) of different capture oligonucleotides in the pool is defined by the formula $P=2^L$. Thus, for example, a hexamer pool, S6 may include $2^6=64$ different capture oligonucleotides, each capture oligonucleotide being defined by the sequence S-S-S-S-S-S, whereby S is G or C. Therefore, a capture pool containing CpG target sequences and/or total nucleotide length between 4 to 10 bases in length and restricted to G+C bases may contain anywhere between 16 different oligonucleotides ($2^4$; S4 pool), 32 different oligonucleotides ($2^5$; S5 pool), 64 different oligonucleotides ($2^6$; S6 pool), 128 different oligonucleotides ($2^7$; S7 pool), 256 different oligonucleotides ($2^8$; S8 pool), 512 different oligonucleotides ($2^9$; S9 pool), and 1024 different oligonucleotides ($2^{10}$; S10 pool).

FIG. 1 depicts the total number of oligonucleotide binding sites in all 27,639 human CpG islands (CGIs) in the UCSC Genome Browser Database (see genome.ucsc.edu and Nucl. Acids Res., 37:D755-D761, 2008; one DNA strand only) collectively represented by each $S_L$ oligonucleotide pool, where L=length of oligonucleotide in bases, and the total number (P) of different oligonucleotides in each pool is $P=2^L$. FIG. 1 also shows the average number of oligonucleotide binding sites per every 200 bp fragment (one strand only). The data shows that CGI-containing fragments can be targeted for pull-down via multiple oligonucleotide binding events on a given polynucleotide fragment. The 27,639 CGIs in the UCSC database are identified in accordance with the CpG island criteria described above, which are further in Gardiner-Garden et al., J. Mol. Biol., 196:262-282, 1987.

FIG. 1 also shows the total number and percentage of human CGIs that can be collectively targeted by a given $S_L$ pool. Thus, when the number of bases in the oligonucleotide pool ($S_L$) is between 4 and 10, 85% to 99.9% of the CGIs in the human genome would be targeted by one or more oligonucleotides in the pool. Increasing the number of bases from 11 to 15 would increase the specificity of individual oligonucleotide bindings, but would decrease the number of oligonucleotide bindings per 200 bp polynucleotide target fragment from 5.09 (S11 pool) to 1.81 (S15 pool), and reduce the percentage of possible CGIs that could be targeted or pulled down from about 79% (S11 pool) to about 49% (S15 pool).

In another embodiment, an oligonucleotide pool for enriching CpG islands is defined by the sequence, 5'-S(2-8)-C-G-3', where S(2-8) represents a stretch of 2 to 8 G or C bases immediately 5' of a CG dinucleotide, and where the number of different oligonucleotides (P) is defined by $P=2^{(L-2)}$, where L=length of each CpG target sequence in the pool (3'-CG included). Accordingly, such pools may employ between 4 and 256 different oligonucleotides for enriching CG dinucleotide-containing polynucleotide targets and for enhancing the ability of bound primers containing CG at the 3'-end to participate in a primer extension process performed in advance of the pull down step.

In another embodiment, the capture oligonucleotides in the capture pool may alternatively include residues other than G or C. For example, in one embodiment, the oligonucleotide pool may be designed to include a consecutive run of cytosine or guanine residues spanning the middle of the CpG target sequence and A, C, G, or T residues in the flanking regions, whereby the consecutive run or G and/or C residues comprises at least 60%, 70%, 80%, 90%, or 100% of the bases in each CpG target sequence or in at least at least 60%, 70%, 80%, 90%, or 100% of all bases in the capture oligonucleotides or capture oligonucleotide pool.

In another embodiment, the oligonucleotides in the capture pool are designed in accordance with a progressive scanning analysis reflecting the composition and proportional number of occurrences for short oligonucleotides, 4 to 10 bases in length for one or more CpG islands. For example, in one embodiment for enriching CGI polynucleotide targets, an oligonucleotide capture pool may be designed using a progressive scanning analysis to progressively scan one or more CGIs (or all CGIs) from a genome source one base at a time for each successive sequence of L bases, where L=4 to 10, and generate one or more "frequency set(s)", each frequency set comprised of a list of sequences of length L, along with the number of sequence occurrences each different sequence. The frequency sets may be derived by scanning all consecutive short sequences of length L in the CGIs regardless of their base sequence, or they may be derived by scanning for all occurrences of a particular base sequence, such as 5'-S (4-10)-3' or other sequences as described below.

From the derived frequency sets, an oligonucleotide capture pool may be assembled, whereby the CpG target sequences or capture oligonucleotides (as a whole) in the capture pool include all of the sequences represented in the frequency set or they may be limited to those sequences occurring in the top 50%, top 30%, top 20%, top 10%, or top 5% with respect to frequency. Depending on the target sequences scanned for and the number of "hits" accorded to each target sequence member in the frequency set, the oligonucleotide may be limited to G or C residues or it may additionally include A and T residues as well. The capture pool may be further modified to include the various individual oligonucleotide members relative to their proportional frequencies relative to other members in the frequency set, including selected members or subsets of members from the frequency set.

In one embodiment for enriching CpG polynucleotide targets, an oligonucleotide capture pool may be designed using a progressive scanning analysis to progressively scan one or more CGIs (or all of the CGIs) from a genome source one base at a time for each successive sequence defined by 5'-N (1-4)-C-G-N(1-4)-3', whereby N(1-4) represents stretches of 1 to 4 A, C, G, or T nucleotides flanking a CG dinucleotide as found in the CGIs. Alternatively, the progressive scanning analysis may be obtained by scanning one or more CGIs (or all of the CGIs) from a genome source, one base at a time, for each successive sequence defined by 5'-N(1-4)-C-G-N(1-4)-3', whereby N(1-4) represents stretches of 1 to 4 C or G nucleotides flanking a CG dinucleotide as found in the CGIs. In this embodiment, the cytosine nucleotide in the CG dinucleotide is positioned in the geometric middle of the CpG target sequence or in a position immediately 5' to the geometric middle of the CpG target sequence (or oligonucleotide). It is believed that the use of such capture pools will ensure enrichment of polynucleotide targets containing CG dinucleotides to facilitate an analysis of their methylation status for a given source of genomic DNA.

In another embodiment for enriching CG-dinucleotide containing polynucleotide targets (as found in CGIs) an oligonucleotide capture pool may be designed using a progressive scanning analysis to progressively scan one or more CGIs (or all of the CGIs) from a genome source one base at a time for each successive sequence defined by 5'-N(1-8)-C-G-3', whereby N(1-8) represents a stretch of 1 to 8 A, C, G, or T bases as found immediately 5' of a CG dinucleotide. Alternatively, the progressive scanning analysis may be obtained by scanning one or more CGIs (or all of the CGIs) from a genome source, one base at a time, for each successive sequence defined by 5'-N(1-8)-C-G-3', whereby N(1-8) represents a stretch of 1 to 8 C or G bases as found immediately 5' of a CG dinucleotide The purpose of these capture pools is to ensure enrichment of polynucleotide targets containing CG dinucleotides and to enhance the ability of bound primers containing CG at the 3'-end to participate in a primer extension process performed in advance of the pull down step.

A capture pool derived from a progressive scanning analysis of CGI sequences may reflect oligonucleotide occurrences present in these regions in their relative proportion to one another. The occurrences or hits may be directed to a pre-determined set of target sequences or they may reflect the actual composition of short sequences in the CGIs. Thus, a listing of oligonucleotide "hit counts" may be constructed from individual members of the pool or frequency set to determine the proportional ratios of individual oligonucleotides to include in the pool. The oligonucleotide capture pool may be assembled, whereby the CpG target sequences or whole capture oligonucleotides in the capture pool are limited to sequences in the CGIs occurring in the top 50%, top 30%, top 20%, top 10%, or top 5% (in frequency) whereby the sequences are restricted to those in a particular degenerate target sequence or pre-determined target sequence set. Alternatively, the CpG target sequences or whole capture oligonucleotides in the capture pool may be limited to sequences in the CpG islands occurring in the top 50%, top 30%, top 20%, top 10%, or top 5% (in frequency) relative to all sequences in the CGI regions analyzed, independent of any pre-determined target sequence set.

In another embodiment, the capture pool may be assembled based on inspection of an oligonucleotide hit count listing displaying the number of occurrences of each oligonucleotide in the CGIs. Such an analysis can facilitate construction of a weight matrix table reflecting frequencies of particular nucleotide residues in particular oligonucleotide positions. A pool of oligonucleotide sequences may be directly synthesized in accordance with these frequencies.

By way of example, FIG. 2A illustrates a position weight matrix table derived from a progressive scanning analysis, which shows the frequencies of nucleotides in positions surrounding a central CG core dinucleotide in a hexamer (6-mer) pool when scanning across all 27,639 CGIs in the UCSC CpG island database. FIG. 2A shows there is a bias for G and C residues in the flanking positions (i.e., positions 1, 2, 5, 6) surrounding the central CG dinucleotide core. In particular, the frequencies of G or C residues in these outer positions range from about 35.5% to 38.6%, which is nearly 2.5 to 3 times the frequencies of A or T residues, which range from 11.6% to 14.5%. In one embodiment, the pool of CGI-targeted oligonucleotide is directly generated on the basis of the frequencies of particular nucleotide residues in particular oligonucleotide positions in a position weight matrix table, as shown in FIG. 2A. Alternatively, a pool of CGI-targeted oligonucleotides may be constructed from individual members of the pool combined in accordance with the ratios in which individual sequences in a degenerate target sequence are found in the CGIs or in accordance with the ratios in which individual short sequences present in the CGIs independent of any pre-selected target sequences or any computational step for filtering out sequences lacking a pre-determined target sequence.

FIG. 2B a position weight matrix analysis table showing the frequencies of nucleotides 5' of a 3-terminal CG dinucleotide in a hexamer (6-mer) pool when scanning across all 27,639 CGIs in the UCSC CpG island database. FIG. 2B shows there is a bias for G and C residues upstream of the terminal CG dinucleotide, similar to the frequencies observed in FIG. 2A. Similarly to FIG. 2A above, a pool of CGI-targeted oligonucleotides may be constructed from individual members of the pool combined in accordance with the ratios in which the individual oligonucleotides are observed in one or more (or all) of the CGIs in a given genomic DNA source by sequence analysis. Alternatively, a pool of CGI-targeted oligonucleotide may be directly generated on the basis of a progressive scanning analysis reflecting the frequencies of particular nucleotide residues in particular oligonucleotide positions when scanning one or more (or all) of the CGIs in a given genomic DNA source (by sequence analysis).

FIGS. 3A and 3B illustrate the selectivity of CpG island binding using various oligonucleotide pools according to the present invention. In particular, FIG. 3A shows total number of oligonucleotide hits (corresponding to the published DNA strand only) for a given oligonucleotide pool., whereby "hits" are defined by the number of times an oligonucleotide sequence from a given capture pool is present in: (1) all 27,639 CGIs in the UCSC CpG island database; (2) in the human genome as a whole; (3) in the human genome following subtraction of the CGIs (CGI masked); (4) in the human repeat regions; (5) in the human genome following subtraction of the repeat regions (repeat masked); (6) in the human genome following subtraction of CGIs and repeats (CGI and repeat masked). In FIGS. 3A and 3B, the total number of base pairs corresponding to each of these six regions is listed in the top row. FIG. 3A presents hit counts corresponding to 14 different oligonucleotide capture pools, each containing a plurality of different capture oligonucleotides between 4 and 10 bases in length. Pools S4 to S10 are restricted to G and C residues as described above. The remainder of the pools are defined by the formula, 5'-S(1-4)-C-G-S(1-4)-3', whereby S(1-4) represents stretches of 1 to 4 C or G nucleotides flanking a CG dinucleotide based on nucleotide position frequencies obtained by scanning across all 27,639 CGIs in the UCSC CpG island database as described above. FIG. 3A shows that the hit counts are progressively reduced as the length of the oligonucleotides in each pool is increased. FIG. 3A further shows that the hit counts are generally higher in other regions as compared to the CGIs. However, the increased hit counts elsewhere are not proportional to the extent of their sequence content; human repeat regions are about 66 times larger in sequence content compared to the CGIs.

FIG. 3B shows the average number of oligonucleotide hits per average 200 bp fragment (one strand only). FIG. 3B shows that the average number of oligonucleotide hits per 200 bp fragment is progressively reduced as the oligonucleotide length in each pool is increased. In general and on average, a 200 bp CpG island fragment will typically contain between about 2 to 44 binding sites, and in many cases between about 4 to about 20 binding sites. In contrast, 200 bp non-CpG island fragments generally contain less than 1 binding site. This data highlights the potential for increased binding of capture oligonucleotides to polynucleotide targets so as to facilitate selective pull-down and enrichment of CpG islands. FIG. 3B further depicts the selectivity of binding to CpG island fragments relative to non-CpG island fragments. This is reflected in the increased numbers of hits per 200 bp of CGI fragments relative to the number of hits in the other regions listed. Further, when subtracting (or masking) the CpG islands or both the CpG islands and the repeat regions from the human genome as a whole, the ratio of oligonucleotides binding to CpG islands as opposed to other regions ranges from a minimum of about 10:1 for the S4 pool up to about 202,652 for the S4-C-G-S4 pool. Thus, the CpG-targeted oligonucleotide capture pools of the present invention may provide a level of enrichment of CGI polynucleotide fragments over non-CGI polynucleotide fragments by a factor of greater than 10:1, greater than 50:1, greater than 100:1 or more.

Bound oligonucleotides may serve as templates for primer extension prior to the pull down step. Further, bound fragments may be additionally subjected to a ligation step to facilitate ligation of adjacently bound oligonucleotides, which may further enhance the ability to pull down hybrids.

The capture oligonucleotides may be comprised of conventional short DNAs. Alternatively, the capture oligonucleotides may include RNAs or unconventional, synthetic oligonucleotide backbones, especially those containing modifications for enhancing hybrid stability when using shorter oligonucleotides (e.g., 4 or 5 bases) for pulling down polynucleotides (Current Protocols in Nucleic Acid Chemistry, Eds. Serge L. Beaucage, et al., John Wiley & Sons, 2004). Accordingly, capture oligonucleotides may include unconventional chemical or backbone additions, substitutions, and/or linkages, including but not limited to amide backbone modifications as in polyamide or peptide nucleic acids (PNA), locked nucleic acids (LNAs), sugar-phosphodiester and phosphotriester linkages, duplex stabilizing stilbene or pyrenyl caps, 2'-O-methyl linkages, guanidine linkers in DNA ("DNG"), S-methylthiourea linkers, methylphosphonate linkages, phosphoramidate linkages, phosphorothioate linkages, phosphonic ester nucleic acid linkages, pyranosyl oligonucleotide linkages, bicyclo- and tricyclo-nucleic acid linkages, formacetal and 3'-thioformacetal linkages, morpholino linkages, or other modifications of the natural phosphodiester internucleoside bond, or combinations of such linkages in a single backbone. The capture oligonucleotides may include a mixture of linkages in the same nucleic acid (e.g., sugar-phosphodiester and 2'-O-methyl linkages) or may have all of one type of linkages (e.g., all 2'-O-methyl or all amide modification linkages). Capture oligonucleotides may contain unconventional nucleic acid structures in whole or in part. Accordingly, they may incorporate or substitute one or more of the naturally occurring nucleotides or bases with an analog; internucleotide modifications incorporating, for example, uncharged linkages (e.g., methylphosphonates, phosphotriesters, phosphoamidates, carbamates, etc.) or charged linkages (e.g., phosphorothioates, phosphorodithioates, etc.); modifications incorporating intercalators (e.g., acridine, psoralen, etc.), chelators (e.g., metals, radioactive metals, boron, oxidative metals, etc.), or alkylators, and/or modified linkages (e.g., alpha anomeric nucleic acids, etc.), including those disclosed in US 2007/0166741, the disclosures of which are incorporated by reference herein.

Preferred unconventional capture oligonucleotides may include one or more bases from RNAs, "locked nucleic acids" (LNAs), peptide nucleic acids (PNAs), or may include duplex stabilizing stilbene or pyrenyl caps. It is believed that use of such unconventional capture oligonucleotides is especially suited for use in shorter (for example, 4-mers) oligonucleotide pools. RNA:DNA hybrids are known to be more stable than DNA:DNA hybrids (Chien and Davidson, Nucl. Acids Res., 5:1627, 1978). PNAs are uncharged nucleic acid analogs for which the phosphodiester backbone has been replaced by a polyamide, which makes PNAs a polymer of 2-aminoethyl-glycine units bound together by an amide linkage. PNAs can provide increased specificity and melting temperature as compared to nucleic acids, capacity to form triple helices, stability at acid pH, non-recognition by cellular enzymes like nucleases, polymerases, etc. (Rey et al., 2000, FASEB J., 14:1041-1060; Nielsen et al., 1999, Curr. Issues Mol. Biol., 1:89-104). LNAs are bicyclic nucleic acids in which a ribonucleoside (including e.g., a furanose ring) is linked between the 2'-oxygen and the 4'-carbon atoms with a methylene unit. Exemplary LNA bases include modified bicyclic monomeric units with a 2'-O-4'-C methylene bridge, such as those described in U.S. Pat. No. 6,268,490, the disclosures of which are incorporated by reference herein. Duplex stabilizing stilbene or pyrenyl caps include trimethoxystilbene and pyrenylmethylpyrrolindol caps (Glen Research, Sterling, Va.).

Capture oligonucleotides may optionally include or be linked to a spacer which may reduce steric hindrance effects negatively impacting upon hybridization of polynucleotides to short capture oligonucleotides linked to nanoparticles or other solid supports. The spacer may also enhance simultaneous binding of short capture oligonucleotides to both an immobilization substrate and a CGI polynucleotide target when using a capture tag, such as biotin, for example. Thus, capture oligonucleotides of the present invention may include a suitable spacer between the capture tag and the oligonucleotide or between the solid support and the oligonucleotide. Inclusion of the spacer is designed to increase the distance between the capture oligonucleotide target sequences and an immobilization substrate or other solid support where the capture oligonucleotides are conjugated thereto.

In one embodiment, the spacer includes a polyethylene glycol-based moiety linked to the oligonucleotide, such as tetra-ethylene glycol (TEG). Alternatively, a nucleotidyl spacer, such as a continuous stretch of 8-30 adenines or 8-30 thymines may be used alone or in combination with the polyethylene glycol-based spacer. The capture oligonucleotides may include or be chemically linked to a spacer at the 5'-end, 3'-end or both, which may or may not be linked to a capture tag. Exemplary spacers may further include, for example, a variety of spacer phosphoramidates for inserting variable length spacer arms and photocleavable spacer modifiers (Glen Research, Sterling, Va.). Spacer compositions and methods for attaching and linking spacers to oligonucleotides, capture tags, and nanoparticles are described in U.S. Pat. Nos. 4,914,210, 4,962,029, 5,888,723, and 6,720,411, the disclosures of which are incorporated by reference herein.

Prior to binding or hybridization, a genomic DNA source of interest is fragmented according to a pre-determined size or size range. The genomic DNA may be selected from any genomic source containing CpG islands, including vertebrate tissues and cell lines, especially humans. The genomic DNA may be fragmented by restriction enzyme digestion or by shearing to produce a set of genomic polynucleotide fragments averaging in size between about 50 bp to about 2000 bp, between about 100 bp to about 500 bp, between about 100 bp to about 300, about 100 bp, about 200 bp, about 300 bp, about 400 bp., about 500 bp etc. For example, genomic DNA may be digested with MseI, a frequent cutter targeting a four-base sequence rarely found in CG-rich regions; thus, most CG-rich CGIs would remain intact whereas the bulk of the genomic DNA would be removed by restriction enzyme cleavage. Preferably the genomic DNA is sheared by sonication, to produce a plurality of genomic fragments having a predefined average size of about 100 bp, 200 bp, 300 bp, 400 bp, 500 bp etc. Conventional shearing methods may be adjusted to produce a desired average size.

In addition, the polynucleotide fragment ends may be modified to facilitate ligation to linkers or adaptors suitable for subsequent modifications or analyses of CGI polynucleotide targets released from the capture oligonucleotides. For example, in one embodiment, the polynucleotide fragments are blunt-ended and ligated to a double stranded adaptor functioning as a primer for extension, bisulfite conversion, and/or sequencing, such as used in the SOLiD™ 3 Plus System (Applied Biosystems Inc., Foster City, Calif.).

In a preferred embodiment, the capture oligonucleotides in the capture pool are bound to the polynucleotide targets under solution-phase conditions in which the oligonucleotides and polynucleotide fragments are freely diffusible relative to one another. Under these conditions, targeted CGI fragments bound to the capture oligonucleotides may be separated and purified from unbound polynucleotide fragments via capture tag-mediated pull-down of the associated polynucleotide targets using an appropriate or complementary immobilization substrate. Thus, for example, biotinylated capture oligonucleotides bound to CGI targets may captured onto streptavidin beads and subsequently released therefrom by heating or other suitable means. The capture tags in the capture oligonucleotides may be bound to the immobilization substrate before binding to the genomic polynucleotide fragments or they may be bound to the immobilization substrate following binding of the capture oligonucleotides to the genomic polynucleotide fragments. Alternatively, the capture oligonucleotides may be directly linked to small beads or nanoparticles, which may be used to recover bound complexes directly as both capture tag and immobilization substrate, or they may be bound to an immobilization substrate suitable for recovery of captured CGI-containing polynucleotide target fragments.

In another embodiment, the capture oligonucleotides may be hybridized under solution-phase conditions to polynucleotide fragments whereby the capture oligonucleotides are attached to nanoparticles that are suspended and freely diffusible in solution (as in a flowable slurry) during hybridization. Individual nanoparticles may be linked to a number of different capture oligonucleotides, including all of the different members of an oligonucleotide pool. The capture oligonucleotides may be directly linked to nanoparticles or small beads or they may be indirectly linked via spacers to avoid potential steric hindrance issues interfering with hybridization as described above.

A nanoparticle may be spherical in shape and may typically have a largest dimension of about 20 nm to 1 micron, or more suitably about 50 to 200 nm. Where the nanoparticles are substantially spherical in shape, the nanoparticles may commonly have a diameter between about 20 to about 500 nm and, between about 50 to about 200 nm, or between about 10 to about 30 nm. Nanoparticles may be typically comprised of a polymeric material containing derivatizable functional groups (e.g., p-aminostyrene polymers and copolymers, and cyanuric chloride activated cellulose) or polymeric material that can be activated (e.g., nylon beads). Suitable materials which can be used to form nanoparticles include nylon, polystyrene, glass, polypropylenes, polystyrene/glycidyl methacrylate latex beads, latex beads containing amino, carboxyl, sulfonic and/or hydroxyl groups, polystyrene coated magnetic beads containing amino and/or carboxylate groups, teflon, and the like.

Methods and compositions for linking oligonucleotides to nanoparticles, including spacers therefore are described in U.S. Pat. No. 6,720,411, the disclosures of which are incorporated by reference herein. Additional nanoparticle compositions and conjugates, including methods for linking oligonucleotides to nanoparticles are disclosed in U.S. Pat. Appl. Nos. 2003/0143604, 2006/0148124, 2006/0177855 and 2009/0036315, the disclosures of which are incorporated by reference herein.

In another embodiment the capture oligonucleotides in the capture pool hybridized to the polynucleotide targets under stationary conditions, whereby the capture oligonucleotides are in a fixed position relative to the freely diffusible polynucleotide targets. In this case, the capture oligonucleotides may be conjugated or attached to a solid phase, solid support, or solid matrix, including, for example, cellulose, polystyrene, polyethylene, polypropylene, polycarbonate; any nanoparticle attached to a solid support; or any solid plastic material configured in the shape or to the shape of a column, plate, slide, dish, cup, strand, chip, strip, microplate, or microarray. A functionalized solid phase such as plastic or glass that has been modified so that the surface contains carboxyl, amino, hydrazide, aldehyde groups, nucleic acid or nucleotide derivatives can also be used. Any solid phase such as plastic, metal, magnetic or glass microparticles, beads, microbeads, nanoparticles, strips, test tubes, slides, strands, chips, microchip or microtiter plates can be used. Where the capture oligonucleotides are attached to a solid support, they may be identifiable, either by their known locations on a solid support, such as a sub-well plate or microarray, or when, for example, conjugated to beads, by a distinguishable colored dye. The means for identifying the capture sequence probes are known in the art.

In another embodiment, the capture oligonucleotides may be bound to cellulose column in a manner analogous to mRNA isolation from Oligo-dT cellulose columns as disclosed, for example, in Aviv et al., PNAS, 69(2):1408-1412, 1972. In this case, polynucleotide fragments bound to capture oligonucleotides in the cellulose column may be eluted from the column by one or more washes in an aqueous low salt buffer having a 1-10 mM monovalent salt concentration, for example.

In another embodiment, short capture oligonucleotides from a capture pool may be attached to a microarray, whereby polynucleotide targets are bound to the capture oligonucleotides and eluted from the microarray as disclosed, for example, in Hodges et al., Genome Res., 19(9):1593-1605, 2009. In particular, bound polynucleotide fragments may be eluted from the microarray under low salt conditions (1-10 mM monovalent salt concentration). In preferred embodiments, capture oligonucleotides from a capture pool will be attached, conjugated, or printed onto the same or substantially the same locations or sites to increase the propensity for pulling down CGI- and other CG-rich or epigenetically informative polynucleotide target fragments. In addition, to reduce steric hindrance effects that may reduce binding of polynucleotides to short capture oligonucleotides affixed to a solid support, the capture oligonucleotides may include a suitable spacer between the capture tag and the oligonucleotide or between the solid support and the oligonucleotide as described above.

As will be appreciated by those of skill in the art, hybridization stringencies and/or wash conditions may be adjusted, depending on the oligonucleotide length, oligonucleotide concentration, and oligonucleotide melting temperature(s). (Tm), where Tm refers to the temperature at which the oligonucleotide is 50% annealed to its exact complement. As shown in FIG. 4, shorter oligonucleotides will have lower melting temperatures; longer oligonucleotides will have higher melting temperatures. Thus, for example, for a DNA/DNA hybrid at an oligonucleotide concentration of 5 µM in 0.5M monovalent salt, a 4 mer, GCGC has a Tm<10° C.; a 6 mer, 5'-CGCGCG-3' has a Tm of 41.4° C.; and a 10 mer, 5'-CGCGCGCGCG-3' (SEQ ID NO. 1) has a Tm of 71.0° C. As the concentration of these same oligonucleotides increases, however, so does the melting temperature. Accordingly, depending on the oligonucleotide concentration, the oligonucleotide length, and the oligonucleotide compositions (including G+C content etc) in the capture pool, as well as the mode of hybridization (solution phase or solid phase), hybridization and wash conditions may be adjusted with respect to temperature, salt concentration, and other variables known to those of skill in the art. Preferably the conditions will be adjusted to maximize binding of multiple short capture oligonucleotides to targeted fragments and to reduce the more sparse binding to non-targeted fragments. Skilled artisans will appreciate that ribonucleic acid (RNA), locked nucleic acid (LNA) and peptide nucleic acid (PNA) residues exhibit tighter binding to complementary DNA bases in polynucleotides. Accordingly, since oligonucleotides containing RNA, LNA, or PNA residues will have higher melting temperatures compared to their DNA analogues. Accordingly, the hybridization and wash conditions employed when using these oligonucleotides may be adjusted accordingly.

Depending on the oligonucleotide pools used, including oligonucleotide length and composition, "high stringency" or "moderate stringency" hybridization/wash conditions may be used. By way of example, high stringency conditions may involve hybridization at about 68° C. in 5×SSC/5×Denhardt's solution/1.0 percent SDS, and washing in 0.2×SSC/0.1 percent SDS at room temperature. Alternatively, they may involve hybridization in 0.5-1.0 M monovalent salt, followed by washes in 0.1 M monovalent salt, or art-recognized equivalents thereof (e.g., conditions in which a hybridization is carried out at 60° C. in 2.5×SSC buffer, followed by several optional washes at 37° C. in a buffer containing a monovalent salt concentration between 1 to 10 mM). Moderate stringency conditions may involve hybridization at about 55° C. in 6×SSC/5×Denhardt's solution/0.5% SDS/100 µg/ml denatured salmon sperm DNA, followed by one or more washes at 37° C. in 1×SSC/0.1% SDS. Of course, the temperature, ionic strength, etc., can be adjusted to accommodate experimental factors such as probe length, probe composition, and the like. The parameters of salt concentration and temperature can be varied to achieve the optimal level of identity (and acceptable level of mismatches) between the capture probes and the target polynucleotides. Guidance regarding such conditions is available in the art, for example, Sambrook et al., Molecular Cloning: A Laboratory Manual, $3^{rd}$ Ed., CSHL Press, 2001), and Current Protocols in Molecular Biology, (John Wiley and Sons, N.Y.) at Unit 2.10.

In one non-limiting example, sheared adaptor-modified polynucleotide fragments (for example, 1 µg) may be denatured and then placed on ice. Hybridization buffer, including monovalent salt, may then be added. The reaction mixture, including 5 µm oligonucleotides in 0.5 M NaCl may be incubated for about 30 min to 1 hr in a range of temperatures, between a temperature of about Tm −5° C. to a temperature equivalent to Tm. To increase the specificity for targeted pull downs, the hybridization temperature may be adjusted between about the Tm and 1-5° C. above Tm, or more. Thus for example, where the Tm is about 42° C., the hybridization temperature may range between about 37° C. to about 48° C.

Following the hybridization/wash steps, the oligonucleotide:polynucleotide hybrids may be subjected to primer extension, ligation, or both. The primer extension and/or ligation steps may enhance the recovery of CGI- and other CG-rich target fragments by increasing the stability and/or extent of double strandedness in the oligonucleotide:polynucleotide hybrids as described above.

Because genomes carry extensive repeat elements that may undesirably increase the background of fragments pulled down by a given oligonucleotide capture pool as illustrated in FIGS. 3A and 3B, it may be advisable in some cases to perform a short renaturation step immediately following the initial denaturation step to selectively promote re-association of repetitive elements so as to effectively remove or reduce the ability of these elements to serve as targets for capture. Renaturation of repeat regions may be achieved by a 2 hr incubation at 65° C. in 0.5 M NaCl following the denaturation step, but prior to the oligonucleotide:polynucleotide hybridization step.

Alternatively, repetitive sequence regions may be masked or blocked from capture by incorporating blocking DNAs enriched for repetitive DNA sequences during or prior to polynucleotide:oligonucleotide hybridization. Thus, denatured polynucleotide fragments may be hybridized with or pre-incubated with blocking reagents, including but not limited to repetitive sequence blocking DNAs, such as Cot-1 DNA® Blocking Reagent (Invitrogen Corp., Carlsbad, Calif.), or with repeat-targeted capture tag-free oligonucleotides in excess and/or using higher repeat-targeted oligonucleotide lengths (using for example, specific 20-40 bp oligonucleotides, or longer) so as to outcompete with the capture oligonucleotides for binding to the undesired repeat regions.

As described above, CGI target fragments bound to the capture oligonucleotides may be separated and purified from unbound polynucleotide fragments via capture tag-mediated pull-down of the associated polynucleotide targets using an appropriate or complementary immobilization substrate. The recovered CGI- and CG-rich fragments, including the CGI targets may be released from the immobilization substrate by heating or other suitable means. The recovered polynucleotides may be enriched for targeted polynucleotide fragments to the extent that the nucleotide content of targeted CGI- or CG-rich polynucleotide fragments (as a function of total polynucleotide bases) outnumbers the nucleotide content of non-targeted polynucleotide fragments by an enrichment factor of greater than 2:1, greater than 5:1, greater than 10:1, greater than 50:1, or greater than 100:1 or more.

The recovered CGI- or CG-rich fragments may be subjected to various analyses. In a preferred embodiment, short oligonucleotides will be used to enrich for CGI- and/or other epigenetically informative CG-rich fragments, which are then subjected to any one of the art-recognized approaches for determining their methylation status.

In a preferred embodiment, the methylation status of the recovered polynucleotide target fragments is determined by DNA sequencing. In one embodiment, the recovered polynucleotide target fragments may be sequenced directly using a methodology adapted for distinguishing methylated residues from unmethylated residues, such as Single Molecule Real Time (SMRT™) DNA sequencing (Pacific Biosciences, Inc., Menlo Park, Calif.).

Alternatively, the methylation status may be determined by DNA sequencing of recovered polynucleotide target fragments subjected to bisulfite conversion, a biochemical process employing a bisulfite reagent to convert unmethylated cytosine to uracil, whereby methylated cytosine residues are preserved. More specifically unmethylated cytosine reacts with bisulfite to form a sulfonated cytosine reaction intermediate prone to deamination thereby resulting in a sulfonated uracil which can be desulfonated to uracil under alkaline conditions. Given that uracil has the base pairing behavior of thymine whereas 5-methylcytosine has the base pairing behavior of cytosine, this biochemical conversion allows for the discrimination of methylated and non-methylated cytosines possible. Accordingly, when modifying CpG-enriched polynucleotide targets, a bisulfite reagent may be used to distinguish methylated sites from unmethylated sites. Exemplary reagents for bisulfite conversion include sodium bisulfite and magnesium bisulfite.

Thus, when subjecting the recovered polynucleotide target fragments to bisulfite conversion, the methylation status of the bisulfate-converted polynucleotide fragments may be determined by any one of a number of DNA sequencing methods known to those of skill in the art. In particular, the enriched polynucleotides may be bisulfite-converted, linearly extended using a polymerase to form extended duplex fragments, and then ligated to one or more linkers or adaptors sufficient for DNA extension, ligation, sequencing, etc.

In another embodiment, the recovered polynucleotide targets are subjected to bisulfite conversion and the methylation status of the bisulfate-converted polynucleotide fragments is determined by hybridization to a microarray.

Other approaches for evaluating the methylation status may rely on the use of ligands targeting methylated cytosines. These approaches may or may not involve the use of bisulfite conversion and/or DNA sequencing. In one embodiment, the recovered polynucleotide targets are incubated with one or more methylation-specific binding proteins to separate methylated polynucleotide targets from unmethylated polynucleotide. For example, CpG-enriched polynucleotide targets may be subjected to a methylated-CpG island recovery assay (MIRA) using one or more methylation-specific binding proteins to separate methylated polynucleotide targets from unmethylated polynucleotide targets as described in U.S. Pat. No. 7,425,415, the disclosures of which are incorporated by reference herein.

In another embodiment, the recovered polynucleotide targets are incubated with one or more antibodies directed against 5-methyl cytidine to separate methylated polynucleotide targets from unmethylated polynucleotide targets. For example, CpG-enriched polynucleotide targets may be subjected to methylated DNA immunoprecipitation (MeDIP) using anti-5-methylcytidine antibodies, as described in U.S. Pat. Appl. No. 2009/0270482, the disclosures of which are incorporated by reference herein.

Further, any of the above-described CpG-enriched polynucleotide target compositions may be applied to a microarray configured for distinguishing methylated sites from unmethylated sites. For example, the microarray may include oligonucleotide or polynucleotide probes for selective hybridization to bisulfite-treated polynucleotide fragments or polynucleotide fragments separated according to their methylation status.

Although the present invention does not rely on PCR to determine methylation status, it does not exclude the use of PCR for determining methylation status. For example, the recovered polynucleotide targets may be subjected to bisulfite conversion, whereby the methylation status is determined by methylation-specific PCR. Exemplary PCR based methods for determining methylation status include but are not limited to methylation specific PCR (MSP), as disclosed in U.S. Pat. No. 5,786,146; Methylation-sensitive Single Nucleotide Primer Extension "Ms-SNuPE" (Gonzalgo and Jones, Nucleic Acids Res. 25:2529-2531, 1997); Combined Bisulfite Restriction Analysis "COBRA" (Xiong and Laird, Nucleic Acids Res. 25:2532-2534, 1997); Methylated CpG island Amplification "MCA" (Toyota et al., Cancer Res. 59:2307-12, 1999, and WO 00/26401A1) and other methods known to those of skill in the art.

In a further aspect, the present invention provides methods for designing and assembling the above described oligonucleotide capture pools for collectively and selectively enriching CGI- and other epigenetically informative CG-rich target fragments using the above-described computational and assembly steps.

In a further aspect, the present invention provides a kit for selective enrichment of CpG islands in accordance with the above-described methods and components. In one embodiment, the kit includes any of the above-described oligonucleotide capture pools for selective enrichment of CGIs in conjunction with one of the following components, including but not limited to immobilization substrate(s), such as streptavidin beads; genomic DNA sources, including normal and diseased tissue samples; DNA isolation reagents, including cell lysing components; restriction enzymes; hybridization reagents, including hybridization buffers and wash solutions; DNA polymerases and reagents suitable for primer extension reactions; including bead compositions for isolation of bound hybrids; bisulfite conversion and/or sequencing reagents, including adaptors; and the like. The capture oligonucleotides may be free, attached to nanoparticles or small beads, attached to a matrix in a microarray, or any of the other described solid supports described above.

When supplied as a kit, any of the various components or reagents may be packaged in separate containers and admixed prior to use with the solid supports of the present invention. Such separate packaging of the components permits long-term storage. Thus, for example, a kit may supply anhydrous oligonucleotides, enzymes and/or enzyme substrates, and buffers for reconstituting any of these reagents. Any buffers designed to maintain a suitable pH under the reaction conditions of the present invention are contemplated. The anhydrous preparations may be lyophilized, in which water is removed under vacuum, freeze-dried, crystallized, or prepared using any other method removing water so as to preserve the activity of the anhydrous reagents. Recipients may be added to these preparations to stabilize these reagents, such as serum albumins or Prionex. In other embodiments, the reagents may be suspended in an aqueous composition comprising, or example, glycerol or other solvents in which the enzymes and/or other reagents are stable.

EXAMPLES

Example 1

Methylation Profiling of CGIs

In an exemplary methylation profiling study, methylation differences in CGIs may be examined between, for example, human ES cell (H9), neural stem cell (H9-derived), and two c-myc transformed neural stem cell lines derived from different fetal brain regions, or any other cell lines or tissue samples of interest.

Bisulfite Sequencing of Oligo-Captured CpG Enriched Regions (bSOCCER).

A strategy for capturing CpG island enrichment and sequencing of bisulfate-treated DNA is illustrated in FIG. 5. One microgram of genomic DNA may be sonicated into fragments using a Covaris E-200 Automated Focused Ultra-Sonicator (Covaris). Sonicated fragments may be size fractionated using Agencourt AMPure magnetic beads (Beckman Coulter Genomics). The sonicated DNA may be blunt-ended with End-It™ DNA-End Repair Kit, dephosphorated by alkaline phosphatase, and ligated to a 100-fold molar excess Adaptor1 [5'PO$_4$-GAGAGTGGAAGAAAGTCCACTCT-3'ddC; (SEQ ID NO. 2)] using the Fast-Link™ DNA Ligation Kit in a 15 µl reaction. The End-It™ DNA-End Repair Kit, Fast-Link™ DNA Ligation Kit, and alkaline phosphatase may be purchased from EPICENTRE Biotechnologies, Inc., Madison, Wis. Sonicated fragments may be purified away from unbound adaptors and other enzymatic substrates using Agencourt AMPure magnetic beads (Beckman Coulter Genomics). Ligation products may be mixed with an equal volume of 1M sodium phosphate buffer, denatured at 96° C. for 5 minutes and incubated 65° C. for 120 minutes to facilitate renaturation of repeat regions to one another. Genomic polynucleotide fragments may be hybridized to 5'-biotinylated NNCGNN oligonucleotides at a concentration 5 µM (Integrated DNA Technologies, Coralville, Iowa) at 37° C. for 30 minutes. To pull down oligonucleotide:polynucleotide fragment hybrids, 0.5 micrograms of Dynabeads (Invitrogen Corp., Carlsbad, Calif.) may be added to the reaction mixture and incubated 15 min at 37° C. Biotinylated DNA coated beads may be separated with a magnet for 2-3 minutes, washed three times with 0.5M sodium phosphate buffer and resuspended in 10 µl TE. Captured DNA fragments may be released by heat at 70° C. for 5 minutes and bisulfite-treated using the EpiTect® Bisulfite kit (Qiagen) by two rounds of the standard conversion. Bisulfite-converted DNA may be eluted with 24 µl of EB buffer, and then mixed with 1 µl extension primer (25 pmol) and 25 µl High Fidelity PCR Master mix (Roche Diagnostics GmbH, Mannheim, Germany). One cycle of extension may be conducted as 94° C. for 3 min, 55° C. for 1 min and 72° C. for 10 min using an extension primer with the sequence, 5'-CTGCCCCGGGT-TCCTCATTCTCT-TCAAAAATAAACTTTCTTCCACTCTC-3' (SEQ ID NO. 3). Pull-down products may be purified (from adaptors or primers, for example) using AgencourtAMPure magnetic beads (Beckman Coulter Genomics) and ligated to 100 pmol of Adaptor2 [5'-PO$_4$-ATCACCGACTGCCCATAGAGAG-GAAAGCGGAGGCGTAGTGG-3'-ddC (SEQ ID NO. 4)] annealed to [5'-CCACTACGCCTCCGCTTTCCTCTC-TATGGGCAGTCGGTGAT-3'; (SEQ ID NO. 45)] using the Fast-Link™ Kit (EPICENTRE Biotechnologies, Madison, Wis.). The ligation products may be purified using Agencourt AMPure magnetic beads (Beckman Coulter Genomics) and sequenced using a high-throughput single-end sequencing protocol employed in the SOLiD™ 3 Plus System (Applied Biosystems Inc., Foster City, Calif.)

Sequence Mapping and Data Analysis.

Sequence alignment may be performed as described previously (Xie et al., Nucl. Acids Res., 37:4331-4340, 2009). Epigenetic alterations may be scored using a bioinformatic pipeline as described in Gu et al., Nat. Methods, 7:133-136, 2010). Sequence reads may be generated to determine the methylation status of the enriched CGI fragments. High-quality sequence reads may be obtained whereby the CGIs are mapped to the human genome. Quantitative and qualitative methylation data may be obtained, and the degree of degree of CGI coverage over the human genome may be determined. With the statistical tools and criteria provided in a previous study (Gu et al., 2010), CpG sites and differentially methylated CGIs may be compared between ES and NSC-H9 derived cells, as well as among NSCs of different origins, or any other cells or tissues.

It is intended that the foregoing detailed description be regarded as illustrative rather than limiting, and that it be understood that it is the following claims, including all equivalents, that are intended to define the spirit and scope of this invention.

The invention claimed is:

1. A method for selective enrichment of CpG island polynucleotide fragments from genomic DNA, the method comprising:
   (a) providing genomic DNA;
   (b) providing an oligonucleotide capture pool comprising a plurality of different capture oligonucleotides, each capture oligonucleotide in said plurality comprising a capture tag, and a CpG target sequence of between 4 and 10 bases in length, each CpG target sequence capable of binding to one of its complementary sequences in the genomic DNA, wherein the capture tag is not a nucleic acid;
   (c) denaturing the genomic DNA to form plurality of denatured polynucleotide fragments;
   (d) incubating the oligonucleotide capture pool with denatured polynucleotide fragments under conditions sufficient to promote targeted binding of the capture oligonucleotides to CG-rich regions of the polynucleotide fragments, wherein at least 60% of the collective bases in the capture oligonucleotides in the capture pool incubated with the denatured polynucleotide targets are cytosine or guanine; and (e) separating and recovering CpG-rich polynucleotide fragments bound to the capture oligonucleotides from unbound polynucleotide fragments to enrich for target CpG island polynucleotide fragments, wherein CpG island polynucleotide fragments map to and contain at least part of a CpG island consisting of a continuous region of genomic DNA that satisfies the criteria of (1) having a frequency of CpG dinucleotides corresponding to an observed/expected ratio greater than 0.6, (2) having a GC content greater than 0.5, and (3) having a length of at least 0.2 kb, where the repeat regions matching these criteria are excluded or masked.

2. The method of claim 1, wherein the CpG target sequence of each capture oligonucleotide in the capture pool is between 5 to 8 bases in length.

3. The method of claim 1, wherein the collective percentage of cytosine and guanine bases in the capture oligonucleotide in the capture pool is selected from the group consisting of 70%, 80%, 90%, 95%, and 100%.

4. The method of claim 1, wherein the collective percentage of cytosine and guanine bases in the capture pool is selected from the group consisting of 70%, 80%, 90%, 95%, and 100%.

5. The method of claim 1, wherein the number (P) of different capture oligonucleotides in the capture pool is defined by the formula $P=2^L$, wherein L is the number of bases of the CpG target sequence, wherein L=4, 5, 6, 7, 8, 9, or 10.

6. The method of claim 1, wherein each capture oligonucleotide in the capture pool is cytosine or guanine, wherein the 3'-terminal dinucleotide in each capture oligonucleotide is CG, and wherein the CpG target sequence of each capture oligonucleotide is between 5 to 8 bases in length.

7. The method of claim 1, wherein each capture oligonucleotide in the capture pool comprises a consecutive run of cytosine or guanine residues spanning the middle of the capture oligonucleotide sequence.

8. The method of claim 1, wherein the capture oligonucleotides in the capture pool are designed in accordance with a progressive scanning analysis of CpG island DNA sequences in a given species genome, wherein the target sequences reflect their composition in the CpG island DNA sequences.

9. The method of claim 8, wherein each capture oligonucleotide in the capture pool comprises at least one CG dinucleotide, wherein the cytosine nucleotide in the CG dinucleotide is positioned in the middle of the capture oligonucleotide or in a position immediately 5' to the middle of the capture oligonucleotide.

10. The method of claim 8, wherein each capture oligonucleotide in the capture pool contains a CG dinucleotide at the 3'-end.

11. The method of claim 8, wherein each capture oligonucleotide in the capture pool comprises a cytosine or guanine residue, and wherein the scanning analysis selects GC-restricted oligonucleotide target sequences for the capture pool that represent the top 50%, the top 30%, or the top 10% of GC-restricted oligonucleotides L bases in length that are present in the CpG islands polynucleotide fragments.

12. The method of claim 1, wherein each capture oligonucleotide in the capture pool includes at least one nucleotide comprising a member of the group consisting of DNA, RNA, LNA, and PNA.

13. The method of claim 1, wherein the capture tag comprises a nanoparticle, biotin, or combination thereof.

14. The method of claim 1, wherein each capture oligonucleotides in the capture pool comprises a spacer.

15. The method of claim 1, wherein bound capture oligonucleotides are subjected to primer extension.

16. The method of claim 1, wherein the capture oligonucleotides are suspended and freely diffusible in solution during hybridization to polynucleotide fragments.

17. The method of claim 1, wherein the capture oligonucleotides in the capture pool are bound to a matrix in a column and wherein polynucleotide fragments bound to the oligonucleotides are eluted from the column using an aqueous medium.

18. The method of claim 1, further comprising a renaturation step following after step (c) to selectively promote enhanced re-association of repetitive elements or comprising hybridization of capture oligonucleotides without capture tags to repetitive elements after step (c) so as to reduce recovery of polynucleotide fragments containing repetitive elements.

19. The method of claim 1, wherein in the recovered CpG-rich polynucleotide fragments the nucleotide content of targeted CpG island polynucleotides or CG-rich polynucleotide fragments outnumbers the nucleotide content of non-targeted polynucleotide fragments by an enrichment factor of greater than 2:1.

20. The method of claim 1, wherein the capture tags are bound to an immobilization substrate prior to recovery of the CpG island polynucleotide fragments.

21. The method of claim 20, where the recovered CpG island polynucleotide fragments are incubated with one or more methylation-specific binding proteins or with one or more antibodies against 5-methyl cytidine to separate methylated polynucleotide targets from unmethylated polynucleotide targets.

22. The method of claim 20, further comprising determining the methylation status in the target CpG island polynucleotide fragments.

23. The method of claim 22, where the methylation status of the recovered target CpG island polynucleotide fragments is determined by DNA sequencing.

24. The method of claim 23, wherein the recovered target CpG island polynucleotide fragments are subjected to bisulfite conversion and the methylation status of the bisulfate-converted polynucleotide fragments is determined by DNA sequencing.

25. The method of claim 22, wherein the recovered CpG island polynucleotide fragments are subjected to bisulfite conversion and the methylation status of the bisulfate-converted polynucleotide fragments is determined by hybridization to a microarray.

* * * * *